United States Patent
Tang et al.

(10) Patent No.: US 11,000,485 B2
(45) Date of Patent: *May 11, 2021

(54) SUBSTITUTED HYDROXYSTILBENES AS AHR AND NRF2 MODULATORS AND THEIR THERAPEUTIC APPLICATIONS

(71) Applicant: Resolvex Pharmaceuticals Inc., Vancouver (CA)

(72) Inventors: Liren Tang, Vancouver (CA); Michael Patrick Allen Lyle, North Vancouver (CA); Youwen Zhou, Vancouver (CA)

(73) Assignee: Resolvex Pharmaceuticals Inc., Vancouver (CA)

( * ) Notice: Subject to any disclaimer, the term of this patent is extended or adjusted under 35 U.S.C. 154(b) by 243 days.

This patent is subject to a terminal disclaimer.

(21) Appl. No.: 16/221,530

(22) Filed: Dec. 16, 2018

(65) Prior Publication Data

US 2019/0117589 A1 Apr. 25, 2019

Related U.S. Application Data

(63) Continuation-in-part of application No. 15/638,208, filed on Jun. 29, 2017, now Pat. No. 10,166,201.

(51) Int. Cl.
| | | |
|---|---|---|
| *A61K 31/05* | (2006.01) | |
| *A61P 25/00* | (2006.01) | |
| *A61P 17/10* | (2006.01) | |
| *A61P 37/00* | (2006.01) | |
| *A61P 1/00* | (2006.01) | |
| *A61P 11/06* | (2006.01) | |
| *A61P 29/00* | (2006.01) | |

(52) U.S. Cl.
CPC ............... *A61K 31/05* (2013.01); *A61P 1/00* (2018.01); *A61P 11/06* (2018.01); *A61P 17/10* (2018.01); *A61P 25/00* (2018.01); *A61P 29/00* (2018.01); *A61P 37/00* (2018.01)

(58) Field of Classification Search
CPC .......... A61K 31/05; A61P 11/06; A61P 17/10; A61P 1/00; A61P 25/00; A61P 29/00; A61P 37/00
See application file for complete search history.

(56) References Cited

PUBLICATIONS

Freshney (Culture of Animal Cells, A Manual of Basic Technique, Alan R. Liss, Inc., 1983, New York, p4) (Year: 1983).*
Jian et al., 2014, Impaired Activation of the Nrf2-ARE Signaling Pathway Undermines H2O2-Induced Oxidative Stress Response: A Possible Mechanism for Melanocyte Degeneration in Vitiligo. J Invest Dermatol, 134(8): 2221-2230.
Agak et al., 2014, Propionibacterium acnes induces an interleukin-17 response in acne vulgaris that is regulated by vitamin A and vitamin D. J Invest Dermatol, 134(2): 366-73.
Ma et al., 2018, Baicalein protects human vitiligo melanocytes from oxidative stress through activation of NF-E2-related factor2 (Nrf2) signaling pathway. Free Radical Biol & Med, 129:492-503.
Cuadrado et al., 2018, Transcription Factor NRF2 as a Therapeutic Target for Chronic Diseases: A Systems Medicine Approach. Pharmacol Rev, 70:348-383.
Zhu L., 2016, AhR functions in lymphocytes: emerging concepts. Trends Immunol, 37(1): 17-31.
Shinde et al., 2018, The Aryl Hydrocarbon Receptor: Connecting Immunity to the Microenvironment. Trends Immunol, 39(12): 1005-1021.

* cited by examiner

*Primary Examiner* — Umamaheswari Ramachandran
(74) *Attorney, Agent, or Firm* — CBM Patent Consulting, LLC

(57) ABSTRACT

It discloses a compound of formula I that inhibits the activities of numerous of protein kinases involving the signaling of inflammatory cytokines, therefore, the compound can be used for treating cancers, autoimmune diseases and inflammatory diseases.

3 Claims, 4 Drawing Sheets

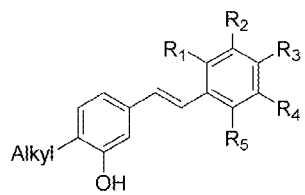

| Compound | Alkyl | R1 | R2 | R3 | R4 | R5 |
| --- | --- | --- | --- | --- | --- | --- |
| 1 | iso-propyl | H | H | H | H | H |
| 2 | iso-propyl | H | H | F | H | H |
| 3 | iso-propyl | F | H | H | H | H |
| 4 | iso-propyl | H | F | H | H | H |
| 5 | iso-propyl | F | H | F | H | H |
| 6 | iso-propyl | F | H | H | H | F |
| 7 | iso-propyl | H | H | CN | H | H |
| 8 | iso-propyl | H | CN | H | H | H |
| 9 | iso-propyl | CN | H | CN | H | H |
| 10 | iso-propyl | H | CN | CN | H | H |
| 11 | cyclopropyl | H | H | H | H | H |
| 12 | cyclopropyl | H | H | F | H | H |
| 13 | cyclopropyl | F | H | F | H | H |
| 14 | cyclopropyl | F | H | H | H | F |
| 15 | cyclopropyl | H | H | CN | H | H |
| 16 | cyclopropyl | H | CN | H | H | H |
| 17 | cyclopropyl | CN | H | CN | H | H |
| 18 | cyclopropyl | H | CN | CN | H | H |
| 19 | cyclopentyl | H | H | H | H | H |
| 20 | cyclopentyl | H | H | F | H | H |
| 21 | cyclopentyl | F | H | F | H | H |
| 22 | cyclopentyl | F | H | H | H | F |
| 23 | cyclohexyl | H | H | H | H | H |
| 24 | cyclohexyl | H | H | F | H | H |
| 25 | cyclohexyl | F | H | F | H | H |
| 26 | cycloheptyl | H | H | H | H | H |
| 27 | cycloheptyl | H | H | F | H | H |

FIG. 1

SUBSTITUTED HYDROXYSTILBENES AS AHR AND NRF2 MODULATORS AND THEIR THERAPEUTIC APPLICATIONS

This application claims priority to U.S. patent application Ser. No. 15/638,208 filed on 29 Jun. 2017 that claimed U.S. patent application Ser. No. 15/338,232 filed 28 Oct. 2016 that claimed U.S. Patent Application Ser. No. 62/407,886 filed 13 Oct. 2016.

TECHNICAL FIELD

The present invention pertains to substituted hydroxystilbenes and their therapeutic applications.

BACKGROUND

The inflammatory response is mediated by cytokines, and cytokine activity and expression in turn are regulated by kinases. Aberrant kinase and cytokine activity play pivotal roles in chronic and acute inflammatory diseases. Aberrant kinase and cytokine activity also underly autoimmune diseases and different types of cancer.

Kinase inhibitors are an established class of anticancer drugs (Chen, J Nat Prod, 2012, 75 (12):2269-2269) and anti-inflammation drugs (Wang et al., J Immunol, 2013, 191(3):1164-1174). For example, Janus Kinase 2 (JAK2) and Janus Kinase 3 (JAK3) are tyrosine kinases that regulate transcription of various target genes involved in growth and proliferation (Reiter et al., Cancer Res, 2005, 65(7):2662-2667; Takemoto et al., Proc Natl Acad Sci USA, 1997, 94(25):13897-13902). JAK2 and JAK3 are also involved in mediating the signaling of many inflammatory cytokines involved in inflammation (Wang et al., J Immunol, 2013, 191(3):1164-1174). JAK2 and JAK 3 inhibitors are therefore useful in treating cancers, and autoimmune and inflammatory diseases (Fridman et al., J Invest Dermatol, 2011, 131(9):1838-1844). p38α (p38 mitogen-activated protein kinase alpha) is a MAP (Mitogen-activated protein) kinase that also mediates the signaling of many inflammatory cytokines involved in inflammation. Inhibitors of the kinase activity of p38 α are therefore useful anti-inflammatory agents (Daniele et al., Cell Signal, 2015, 27(8):1609-1629). Glycogen synthase kinase 3 beta (GSK3β) is a serine-threonine kinase that regulates p53 function in proliferating cells such as cancer cells (WO2006/006939) and its inhibition down regulates inflammatory cytokines (Li et al., Cell Physiol Biochem, 2013, 32(6):1720-1728). Lymphocyte-specific protein tyrosine kinase (LCK) is a Src tyrosine kinase involved in T cell activation and proliferation (Hanke et al., Inflamm Res, 1995, 44:357; Bolen et al., Ann Rev Immunol, 1997, 15:371). LCK inhibition has been successful in treatment of inflammatory diseases (Brisslert et al., Biochem Biophys Acta, 2014, 1842(11):2049-2059). Inhibition of the IκB kinase (IKK) β subunit of the IKK kinase enzyme complex has also been associated with anti-inflammatory effects (Novoselova et al., Mediators Inflamm, 2014, 2014:724838). CLK (CDC2-like kinase) plays important roles in gene splicing and is a potential therapeutic target for Alzheimer's disease (Jain et al., Curr Drug Targets, 2014, 15(5):539-550).

Cytokines play important roles in initiating and regulating immune responses, and therefore their inhibition is a well-established approach to controlling autoimmune and inflammatory diseases (Kopf et al., Nature Reviews Drug Discovery, September 2010, 9:703-718). Exemplary cytokine targets include Interleukin-1β (IL-1β) (Xu et al., Clin Exp Pharmacol Physiol, 2015, 42(10): 1075-83), Interleukin-2 (IL-2) (Roediger et al., J Allergy Clin Immunol, 2015, 136(6):1653-63), Interleukin-6 (IL-6) (Scheller et al., Biochem Biophysica Acta (BBA)—Molecular Cell Research, May 2011, 1813(5):878-888), Interleukin-8 (IL-8) (Aghazarian et al., Urology, 2015, 86(1):52-56), Interferon gamma (IFN-γ) (Di Bari, Clin Ter, 2015, 166(3)), Tumor necrosis factor alpha (TNF-α) (Roubille et al., Ann Rheum Dis, 2015, 74(3):480-489), and Macrophage Inflammatory Protein 1α (MIP-1α) (Dapunt, Mediators Inflamm, 2014, 2014:728619).

PDE4 inhibition is known to improve therapeutic treatment of a number of inflammatory, respiratory and allergic diseases and conditions (U.S. Pat. No. 6,649,633B2; Keren et al., J Dermatol Sci, January 2015, 77(1):74-76).

Novel and improved compounds and compositions for treating cancers, autoimmune diseases and inflammatory diseases are desirable.

BRIEF DESCRIPTION OF DRAWINGS

The accompanying drawings illustrate non-limiting example embodiments of the invention.

FIG. 1 describes the constituents of compounds according to embodiments of the invention.

DETAILED DESCRIPTION

Figure 2:
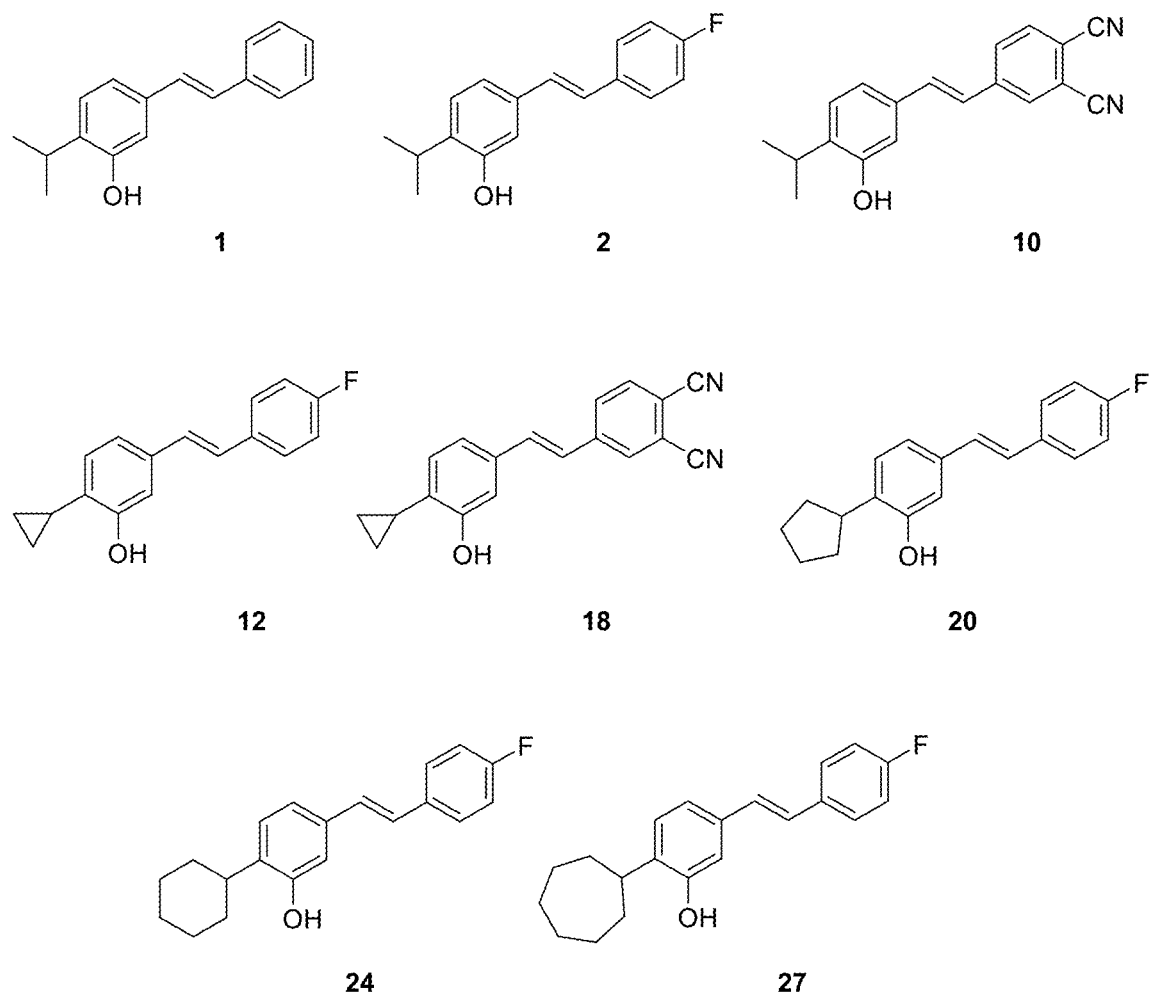
FIG. 2 shows the structures of compounds according to embodiments of the invention.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than in a restrictive sense.

The term "autoimmune disease" as used herein refers to the physiological condition in mammals that is typically characterized by the immune system's reaction to inappropriate targets such as normal tissues. The term "autoimmune disease" includes Addison's disease, ankylosing spondylitis, celiac disease, Hashimoto's thyroiditis, multiple sclerosis, myasthenia gravis, pemphigus, rheumatoid arthritis, Sjogren syndrome, systemic lupus erythematosus, Type 1 diabetes, IBD, psoriasis, vitiligo, alopecia areata and vasculitis.

The term "cancer" as used herein refers to the physiological condition in mammals that is typically characterized by unregulated cell growth. The term "cancer" includes cancer of any origin, including benign and malignant cancers, metastatic and non-metastatic cancers, and primary and secondary cancers. The term "cancer" includes reference to cancer cells. Examples of cancers include, but are not limited to, cancers of the bladder, bone, brain/CNS, breast, cervix, colon, duodenum, esophagus, eye, gall bladder, heart, kidney, larynx, liver, lung, mouth, ovary, pancreas, pharynx, prostate, rectum, stomach, testis, uterus, as well as AIDS-related cancers, Hodgkin's disease, non-Hodgkin's lymphoma, multiple myeloma, melanoma, leukemia (including lymphocytic leukemia, hairy cell leukemia, and acute myelogenous leukemia), choriocarcinoma, rhabdomyosarcoma, and neuroblastoma.

The term an "effective amount" as used herein refers to the amount of active agent sufficient to elicit a desired biological response or, equivalently, to inhibit an undesired biological response. An amount of a particular active agent that is effective may vary depending on such factors as the desired biological response, severity of the disease, the activity of the active agent to be delivered, the route of administration, the rate of excretion of the active agent being employed, the duration of the treatment, other drugs, compounds or materials used in combination with the particular active agent employed, the subject's age, sex, weight, condition, general health and prior medical history of the subject, and like factors well known in the medical arts. In general, an "effective amount" will be that amount of the active agent that is the lowest dose effective to produce the desired biological response. Such an "effective amount" will generally depend upon the factors described above. Generally, an "effective amount" will range from about 1 to about 400 mg per kilogram of body weight per day, more preferably from about 10 to about 50 mg per kg per day. If desired, daily dosage in an "effective amount" may be administered as one dose, or two, three, four, five, six or more sub-doses administered separately at appropriate intervals throughout the day, optionally, in unit dosage forms.

The term "inflammatory disease" as used herein refers to the physiological condition in mammals that is typically characterized by the immune system's excessive reaction to innocuous targets or reaction to inappropriate targets. The term "inflammatory disease" includes Alzheimer's disease, amyotrophic lateral sclerosis, asthma, atherosclerosis, atopic dermatitis, autoimmune diseases, eczema, inflammatory bowel disease, interstitial cystitis, irritable bowel syndrome, osteoarthritis, Parkinson's disease, periodontal disease, psoriasis and sun burn.

The term a "package insert" as used herein refers to instructions customarily included in commercial packages of medicaments that contain information about the indications, usage, dosage, administration, contraindications, other medicaments to be combined with the packaged product, and/or warnings concerning the use of such medicaments, and the like.

The term "pharmaceutically acceptable carrier" as used herein refers to one or more excipients, stabilizers, fillers, binders, humectants, disintegrating agents, solution retarding agents, absorption accelerators, wetting agents, absorbents, lubricants, coloring agents, diluents, emulsifiers, preservatives, solubilizing agents, suspending agents and the like that are suitable for use with the subject being exposed thereto at the dosages and concentrations employed without undue adverse side effects (such as toxicity, irritation, and allergic response) commensurate with a reasonable benefit/risk ratio. Examples of pharmaceutically acceptable carriers include water, citrate or phosphate buffers, starches, lactose, sucrose, glucose, mannitol, carboxymethylcellulose, alginates, gelatin, polyvinyl pyrrolidone, glycerol, agar, calcium carbonate, alginic acid, sodium carbonate, paraffin, quaternary ammonium compounds, cetyl alcohol, glycerol monostearate, kaolin and bentonite clay, talc, calcium stearate, magnesium stearate, polyethylene glycols, sodium lauryl sulfate, ethyl alcohol, isopropyl alcohol, ethyl carbonate, ethyl acetate, benzyl alcohol, benzyl benzoate, propylene glycol, 1,3-butylene glycol, oils, tetrahydrofuryl alcohol, fatty acid esters, thioxylated isostearyl alcohols, polyoxyethylene sorbitol and sorbitan esters, microcrystalline cellulose, aluminum metahydroxide, and tragacanth, and mixtures thereof and other ingredients that are well known to those skilled in the art.

The term "pharmaceutically acceptable salt" as used herein, refers to toxicologically compatible organic or inorganic salts of the active agent. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, alkali metal (e.g., sodium and potassium) salts, alkaline earth metal (e.g., magnesium) salts, and ammonium salts. A pharmaceutically acceptable salt can have one or more charged atoms and/or one or more counter ion. If the active agent is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the active agent is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The term "proliferative disease" as used herein, refers to the physiological condition in mammals that is characterized by the excessive proliferation of cells and turnover of cellular matrix. The term "proliferative disease" includes cancer, graft-versus-host disease, restenosis, hamartoma syndromes (e.g., tuberous sclerosis or Cowden Syndrome), encephalomyelitis, arthritis, scleroderma, pulmonary fibrosis, renal fibrosis, cystic fibrosis, pulmonary hypertension, hypertrophic cardiomyopathy, Parkinson-White syndrome and wet and dry macular degeneration.

The term "subject" as used herein, refers to an individual to whom an active agent is to be delivered, e.g., for treatment purposes. The term "subject" includes mammals, in particular humans, and other mammals including companion animals such as cats and dogs, livestock animals such as cows, pigs, horses, sheep and goats, zoo animals, and research animals, such as rodents. The "subject" also includes in vitro cultured cells.

The terms "treat", "treating" and "treatment" as used herein refers to an approach for obtaining desired clinical results. Desired clinical results can include, but are not limited to, reduction or alleviation of at least one symptom of a disease. For example, treatment can be diminishment of at least one symptom of disease, diminishment of extent of disease, stabilization of disease state, prevention of spread of disease, delay or slowing of disease progression, palliation of disease, diminishment of disease reoccurrence, remission of disease, prolonging survival with disease, or complete eradication of disease.

Abbreviations

AhR: Acryl hydrocarbon receptor
AKT1: RAC-alpha serine/threonine-protein kinase
CLK4: CDC2-like kinase 4
COPD: chronic obstructive pulmonary disorder
DAI: Disease activity index
DCM: Dichloromethane
DMF: Dimethyl fumarate
DPPE: Diphenylphosphinoethane
DSS: Dextran sodium sulphate
EAE: Experimental autoimmune encephalomyelitis
ELISA: Enzyme-linked immunosorbent assay
FBA: Fetal bovine serum
G-CSF: Granulocyte colony stimulating factor
GM-CSF: Granulocyte macrophage colony stimulating factor
GSK3β: Glycogen synthase kinase 3 beta
IBD: Inflammatory bowel disease
ICAM-1: Intercellular adhesion molecule 1
IFN-γ: Interferon gamma
IKKβ: Inhibitor of nuclear factor kappa-B kinase subunit beta
IL-1α: Interleukin 1 alpha
IL-1β: Interleukin-1 beta
IL-2: Interleukin-2
IL-8: Interleukin-8
IL-17 A/F: Interleukin 17 A/F
JAK2: Janus Kinase 2
JAK3: Janus Kinase 3
LCK: Lymphocyte specific protein tyrosine kinase
MAP: Mitogen-activated protein
MIP-1α: Macrophage inflammatory protein 1 alpha
MS: Multiple sclerosis
Nrf2: Nuclear erythroid 2-related factor
PBMC: Peripheral blood mononuclear cell
p38α: p38 mitogen activated protein kinase alpha
p38β: p38 mitogen activated protein kinase beta
PDE4: Phosphodiesterase 4
PDE4B1: Phosphodiesterase 4B1
PHA: Phytohaemagglutinin
PMA: Phorbol 12-myristate 13-acetate
RA: Rheumatoid arthritis
SYK: Spleen tyrosine kinase
THF: Tetrahydrofuran
TNF-α: Tumor necrosis factor alpha
VCAM-1: Vascular cell adhesion molecule 1

Aspects relate to a compound having Formula I:

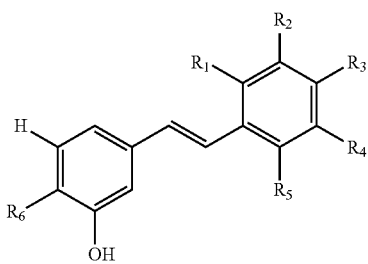

Formula I wherein:
$R^1$ is selected from H, halogen and CN;
$R^2$ is selected from H, halogen and CN;
$R^3$ is selected from H, halogen and CN;
$R^4$ is H;
$R^5$ is selected from H, halogen and CN; and
$R^6$ is alkyl or cycloalkyl,
or a pharmaceutically acceptable salt thereof.

In some embodiments, the compound may be one of exemplary Compounds 1 to 27 set out in FIG. 1. FIG. 2 shows the structure of exemplary Compounds 1, 2, 7, 10, 12, 18, 20, 24 and 27.

In some embodiments, the compound may have Formula I wherein $R^1$ is selected from H, F and CN; $R^2$ is H or CN; $R^3$ is selected from H, F and CN; $R^4$ is H; $R^5$ is H or F; and $R^6$ is selected from iso-propyl, cyclopropyl, cyclopentyl, cyclohexyl and cycloheptyl.

In some embodiments, the compound may have Formula I wherein $R^1$ is H; $R^2$ is H or CN; $R^3$ is selected from H, F and CN; $R^4$ is H; $R^5$ is H; and $R^6$ is selected from iso-propyl, cyclopropyl, cyclopentyl, cyclohexyl and cycloheptyl.

In some embodiments, the compound may have Formula I wherein $R^1$ is H; $R^2$ is H; $R^3$ is F; $R^4$ is H; $R^5$ is H; and $R^6$ is selected from iso-propyl, cyclopropyl and cyclopentyl.

In some embodiments, the compound may be 3-hydroxy-4-isopropyl-4'-fluoro-(E)-stilbene.

In some embodiments, the compound having Formula I may be provided as a pharmaceutically acceptable salt.

Aspects relate to compositions comprising a compound having Formula I and a pharmaceutically acceptable carrier. In some embodiments, compositions comprising compounds of Formula I may be provided in unit dosage form. The amounts of compounds of Formula I that can be combined with a pharmaceutically acceptable carrier to produce a single dosage form will generally be the amount that produces a therapeutic effect. In some embodiments, out of one hundred percent, this amount will range from about 0.1 percent to about 99 percent of active agent, from about 5 percent to about 70 percent of active agent, or from about 10 percent to about 30 percent of active agent.

Aspects relate to methods of treating a condition by administration to a subject of an effective amount of a compound having Formula I. While it is possible for compounds of Formula I to be administered alone, it may be preferable to administer them in combination with one or more pharmaceutically acceptable carriers as a composition. In some embodiments, the methods comprise administering to the subject at least one compound having Formula I either alone in or in combination with at least one additional therapeutic agent. As demonstrated below, compounds having Formula I inhibit cell proliferation, inhibit PDE4, inhibit a range of kinases, and inhibit a range of cytokines. As such, a variety of diseases may be treated with compounds having Formula I. Suitable diseases that may be treated include cancers, autoimmune diseases and inflammatory diseases.

The subject to be treated may be any subject diagnosed as having one of the indicated conditions. The subject to be treated may be in need of treatment for one of the indicated conditions because of a diagnosis of the condition or because of an assessment of risk for developing the condition. The subject may be diagnosed with the condition using diagnostic or clinical tests that are well known. Different diagnostic or clinical tests may be used to diagnose different diseases. The diagnostic tools include, without limit, physical examination, patient and family history, screening tests, laboratory tests, imaging tools, physical tests, cognitive tests, and the like.

In some embodiments, the administration route of compounds of Formula I, alone or in a composition, in terms of effect may be local or systemic (enteral or parenteral), and in terms of location may for example be buccal, epicutaneous, epidural, intraartciular, intracardiac, intracavernous, intracerebral, intracerebroventricular, intradermal, intramuscular, intraosseous, intraperitoneal, intrathecal, intrauterine, intravaginal, intravenous, intravesical, intravitreal, nasal, oral, rectal, subcutaneous, sublingual, sublabial, transdermal, transmucosal, and the like.

In some embodiments, oral administration may be in the form of capsules, cachets, pills, tablets, lozenges, pastes, powders, granules, or as a solution or a suspension in an aqueous or non-aqueous liquid, or as an oil-in-water or water-in-oil liquid emulsion, or as an elixir or syrup, or as pastilles or as mouth washes and the like. In some embodiments, compositions in solid dosage forms for oral administration include capsules, tablets, pills, dragees, powders, granules and the like. The solid dosage forms may be scored or prepared with coatings and shells, such as enteric coatings and other coatings. They may also be formulated so as to provide slow or controlled release of compounds of Formula I. In some embodiments, compositions in liquid dosage forms for oral administration include emulsions, microemulsions, solutions, suspensions, syrups and elixirs. In some embodiments, topical or transdermal administration may be in the form of powders, sprays, ointments, pastes, creams, lotions, gels, solutions, controlled-release patches and inhalants. In some embodiments, parenteral administration (e.g. intravenous administration) may be in the form of solutions in physiologically compatible buffers.

Regardless of the route of administration selected, in some embodiments compounds of Formula I are formulated into pharmaceutically acceptable dosage forms by conventional methods.

Aspects relate to a kit comprising compounds of Formula I, and a package insert comprising instructions for using compounds of Formula I to treat a condition in a subject. Suitable conditions that may be treated include cancers, autoimmune diseases and inflammatory diseases.

EXAMPLES

The invention can be further understood by reference to the following examples, which are provided by way of illustration and are not meant to be limiting.

Example 1

Figure 3:
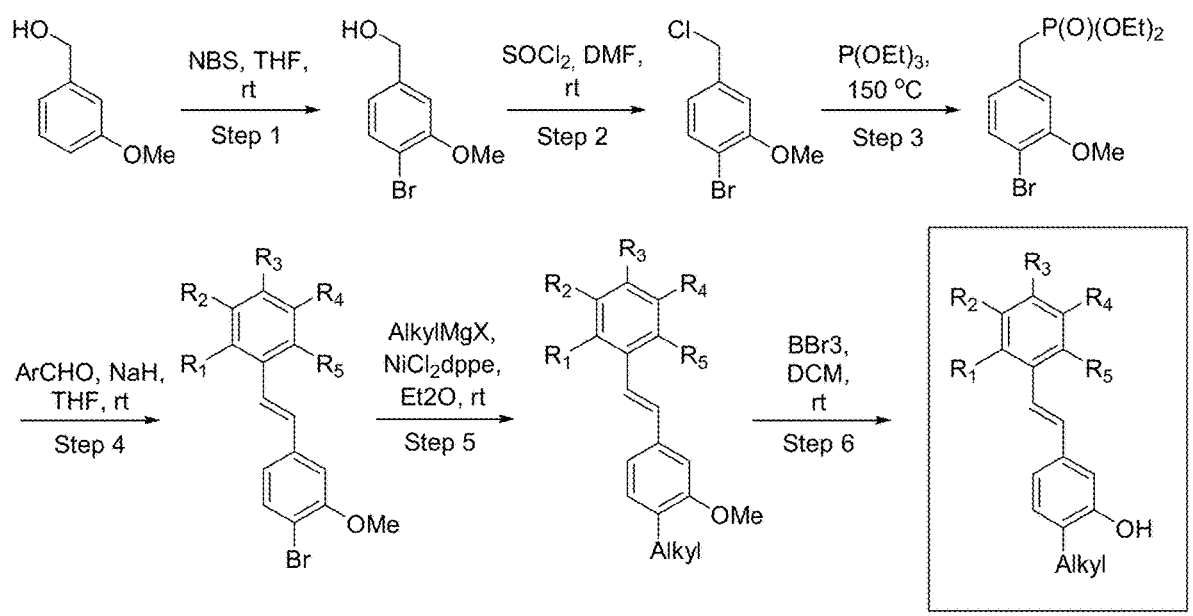
FIG. 3 shows the synthetic process for making compounds according to embodiments of the invention.

FIG. 3 illustrates a synthetic method used to prepare compounds of Formula I according to an embodiment of the invention. The compounds are synthesized in six steps from the commercially available starting material, 3-methoxybenzyl alcohol, as follows.

Step 1: 3-Methoxybenzyl alcohol was brominated with one molar equivalent of N-bromosuccinimide in tetrahydrofuran (THF) at room temperature to afford 4-bromo-3-methoxybenzyl alcohol.

Step 2: 4-bromo-3-methoxybenzyl alcohol was converted to the corresponding benzyl chloride with an excess of thionyl chloride in dimethylformamide (DMF) at room temperature.

Step 3: The benzyl chloride from Step 2 was converted to diethyl 4-bromo-3-methoxybenzylphosphonate with an excess of triethyl phosphite upon heating at 150° C. for 16 hours.

Step 4: The diethyl 4-bromo-3-methoxybenzylphosphonate from Step 3 was reacted with an excess of sodium hydride and a substituted benzaldehyde in THF to afford the substituted trans-4-bromo-3-methoxystilbene (Horner-Wadsworth-Emmons Reaction).

Step 5: The substituted trans-4-bromo-3-methoxystilbene from Step 4 was reacted with an alkyl Grignard reagent in the presence of a catalytic amount of $NiCl_2DPPE$ (diphenylphosphinoethane) in diethyl ether at room temperature to afford the corresponding substituted trans-4-alkyl-3-methoxystilbene (Nickel(II)-catalyzed Kumada Cross Coupling Reaction).

Step 6: The substituted trans-4-alkyl-3-methoxystilbene from Step 5 was reacted with an excess of boron tribromide in dichloromethane (DCM) at room temperature to afford the substituted trans-4-alkyl-3-hydroxystilbene.

Example 2

The synthetic procedure for 3-hydroxy-4-isopropyl-4'-fluoro-(E)-stilbene (Compound 2) according to an embodiment of the invention is presented below. All compounds of the invention may be prepared using this process.

4-Bromo-3-methoxybenzyl Alcohol

To a solution of 3-methoxybenzyl alcohol (20.0 g, 145 mmol) in THF (400 mL) was added N-bromosuccinimide (26 g, 146 mmol) and the resultant mixture was stirred at room temperature for 8 h. Ether (500 mL) was added and the mixture was washed with water (3×100 mL). The solution was dried over magnesium sulfate and concentrated to afford the title compound (31.2 g, 99%) which was used as such for the next step.

Diethyl 4-bromo-3-methoxybenzylphosphonate

To a solution of 4-bromo-3-methoxybenzyl alcohol (31.0 g, 143 mmol) in DMF (200 mL) at 0° C. was added thionyl chloride (17.5 mL, 241 mmol) dropwise over the course of 20 minutes. The resultant mixture was allowed to warm to room temperature and stirring was continued for 24 hours. The reaction was quenched with water and extracted with ether. The combined organic extracts were washed with water and dried over magnesium sulfate before being concentrated in vacuo. The residue was taken up in triethylphosphite (200 mL) and the solution was heated to 150° C. for 4 hours. Excess triethylphosphite was removed in vacuo to afford the crude product which was purified by vacuum distillation to afford the title compound as a colorless oil which solidified upon standing (34.7 g, 72%).

4-Bromo-5-methoxy-4'-fluoro-(E)-stilbene

To a stirred solution of diethyl (4-bromo-3-methoxybenzyl) phosphonate (13.50 g, 40.0 mmol) and 4-fluorobenzaldehyde (5.68 g, 40.0 mmol) in THF (125 mL) at room temperature was added an aqueous solution of sodium hydroxide (50%, 8.0 mL) drop-wise over the course of 30 minutes. The resultant solution was allowed to stir overnight. The reaction mixture was treated with water (200 mL) and extracted with ethyl acetate. The combined organic extracts were dried over magnesium sulfate and concentrated in vacuo to afford the crude product which was purified by recrystallization from hexanes to afford the title compound as a white crystalline solid (9.8 g, 80%).

3-Methoxy-4-isopropyl-4'-fluoro-(E)-stilbene

To a solution of 4-bromo-5-methoxy-4'-fluoro-(E)-stilbene (1.5 g, 4.9 mmol) in ether (30 mL) was added [1,2-bis(diphenylphosphino)ethane] dichloronickel(II) (52 mg, 0.098 mmol). A solution of isopropylmagnesium chloride in THF (2.0 M, 2.7 mL, 5.4 mmol) was then added drop-wise over the course of 5 minutes and the resultant solution was allowed to stir for 24 hours. The reaction mixture was quenched with water (5 mL), diluted with additional ether (60 mL) and the resultant mixture was washed first with a saturated aqueous solution of sodium thiosulfate and then with water. The organic layer was dried over anhydrous magnesium sulfate and concentrated in vacuo to afford the crude product which was purified by recrystallization from hexanes to afford the title compound as a light yellow crystalline solid (874 mg, 66%).

3-Hydroxy-4-isopropyl-4'-fluoro-(E)-stilbene

To a solution of 3-methoxy-4-isopropyl-4'-fluoro-(E)-stilbene (500 mg, 1.85 mmol) in DCM (45 mL) was added boron tribromide (1.4 mL, 15 mmol) and the resultant mixture was stirred for 2 hours. The reaction was quenched by the slow addition of water and was extracted with DCM. The combined organic extracts were dried over magnesium sulfate and concentrated in vacuo to afford the crude product which was purified by recrystallization from hexanes to afford the title compound as a white crystalline solid (327 mg, 69%).

Example 3—Effects on Cell Viability

Cells were cultured in RPMI-1640 containing 10% FBS (Jurkat and THP-1) or DMEM containing 10% FBS (A549 and MDA-MB-435). On Day 1, $1\text{-}5\times10^4$ cells per well in 100 µL of the cell culture medium containing 0.5% FBS were seeded into a 96-well flat bottom plate. On Day 2, the test compounds were added to the culture at different concentrations in triplicates. The controls include triplicates of no compound treatment and cell culture medium without cells. The cells were incubated at 5% $CO_2$, 37° C. for 48 hours. On Day 4, MTS reagent was added to each well and incubated at 37° C. for 4 hours. The absorbance was read at 490 nm. The percentage of inhibition was calculated using the formula: [1-(experiment reading-background reading)/(negative control reading-background reading)]×100. The determined cell viability $IC_{50}$ values are listed in Table 1.

TABLE 1

Cell Viability $IC_{50}$ Values of Compounds against MB435, Jurkat, THP1 and A549 Cells.

| Compound | MDA-MB-435 (µM) | Jurkat (µM) | THP1 (µM) | A549 (µM) |
|---|---|---|---|---|
| 1 | 25 | 2.16 | 2.25 | n.d. |
| 2 | 24.92 | 7.6 | 3.15 | 45 |
| 17 | 1.78 | 7.98 | 2.74 | n.d. |
| 18 | 1.27 | 3.28 | 2.4 | n.d. |
| 12 | 1.62 | 1.65 | 15.42 | 32 |
| 21 | 1.95 | 3.73 | 6.93 | n.d. |
| 24 | 0.39 | 2.66 | 7.18 | n.d. |
| 22 | 1.72 | 2.96 | 2.46 | n.d. |

Example 4—Effects on Cell Proliferation

Cells were cultured in RPMI-1640 containing 10% FBS (Jurkat) or DMEM containing 10% FBS (MDA-MB-435). On Day 1, $1\times10^4$ cells were seeded into one well of a 96-well white ISOPLATE™ with 0.5% FBS. The cells were cultured at 5% $CO_2$, 37° C. overnight. On Day 2, the diluted test compounds were added into each well in a total volume of 100 µL of cell culture medium. For each cell line were set up three wells containing cells and only diluted DMSO as a negative (vehicle) control, and three wells without cells but containing the same volume and type of cell culture medium as background control. The cells were incubated at 5% $CO_2$, 37° C. for 24 hours. On Day 3, 1 µL of [$^3$H]-thymidine was added into each well and incubation at 5% $CO_2$, 37° C. was continued for another 24 hours. On Day 4, 30 µL of 50% TCA was added into each well and was incubated at 4° C. for 4 hours. Plates were washed with $ddH_2O$ four times and then air dried for 30 minutes followed by the addition of 100 µL of scintillation fluid into each well. The radioactivity was read using MICROBETA TRILUX™. The percentage of inhibition was calculated using the formula [1-(experiment reading-background reading)/(negative control reading-background reading)]×100. The determined anti-proliferation $IC_{50}$ values are shown in Table 2.

TABLE 2

Anti-proliferation $IC_{50}$ Values of Compounds against MB435 and Jurkat Cells.

| Compound | MDA-MB-435 (µM) | Jurkat (µM) |
|---|---|---|
| 2 | 6.02 | 1.67 |
| 17 | 1.66 | 1.38 |
| 11 | 4.25 | 1.71 |
| 21 | 1.77 | 0.69 |

Example 5—Effects on Protein Kinase Activities

Kinase profiling was conducted using different recombinant kinase targets against the compounds at 5 uM ATP. The kinases tested included AKT1 (RAC-alpha serine/threonine-protein kinas 1), JAK2, JAK3, p38α, p38β (p38 mitogen-activated protein kinase beta), GSK3β, SYK (Spleen tyrosine kinase), LCK, IKKα and IKKβ and CLK4. The test compounds were tested at 5 µM and 50 µM in triplicates. The results are shown in Table 3.

TABLE 3

Effects of Compounds on Tested Kinase Activities.

| Target | 5 µM CMPD 2 | 50 µM CMPD 2 |
|---|---|---|
| AMPK (A1/B1/G1) | − | +++ |
| AKT1 | − | − |
| JAK2 | − | +++ |
| JAK3 | − | + |
| p38 α | − | +++ |
| p38 β | − | + |
| GSK3 β | − | +++ |
| SYK | − | − |
| LCK | − | ++ |
| IKK α | − | − |
| IKK β | − | ++ |
| CLK4 | +++ | +++ |

Where "−" is less than 20% inhibition, "+" is 20-30% inhibition, "++" is 31-50% inhibition, "+++" is greater than 50% inhibition.

Example 6—Effects on Phosphodiesterase 4 (PDE4) Activity

Assays were performed using recombinant human PDE4B1 enzyme expressed in a baculoviral system. The radiometric assay is a modification of the 2-step method of Thompson and Appleman (Biochemistry 10, 1971, 311-316). The reactions were performed at 1 µM of cAMP. The test articles were each tested at 0.2 µM and 20 µM in triplicates. The percentage inhibition values for the reference inhibitor, rolipram, were also determined and compared to historical assay values to ensure it was in an acceptable range. The results are shown in Table 4.

TABLE 4

Inhibitory Activities on PDE4B1 Enzyme.

| Compound | 0.2 µM | 20 µM |
| --- | --- | --- |
| 2 | + | +++ |
| 12 | + | +++ |
| 20 | + | +++ |
| 27 | + | +++ |
| Rolipram | +++ | +++ |

Where "−" is less than 15% inhibition, "+" is 15-30% inhibition, "++" is 31-50% inhibition and "+++" is greater than 50% inhibition

Example 7—Effects on Human Cytokine Production

Commercially available PBMC cells were used to test the effects of the compounds on the production multiple cytokines. Around one hundred million human PBMC ($1 \times 10^8$) were thawed in a 37° C. water bath and recovered by culturing for 3 hours in RPMI 1640 with 10% fetal bovine serum (FBS) at 37° C. in a $CO_2$ incubator. Cytokine production was induced with a combination of PMA and PHA 30 minutes post the compound treatments. Cells were treated with various concentrations of the compounds for 24 hours at 37° C. To determine the cytokine production secreted into the culture medium by PBMC cells, the culture supernatants were collected from drug-treated or control samples. Commercial ELISA kits (QIAGEN™ ELISAarray Kits) were used for the quantitation. Cytokines tested include: IL-1α, IL-1β, IL-2, IL-4, IL-5, IL-6, IL-8, IL-10, IL-12, IL-13, IL-17A, IFN-7, TNF-α, G-CSF (Granulocyte-colony-stimulating factor), GM-CSF (Granulocyte-macrophage colony-stimulating factor), TGF-β1 and MIP1α. The effects of the compounds on those cytokines demonstrated to be consistently stimulated by phorbol 12-myristate 13-acetate (PMA) and polyhydroxy fatty acid (PHA) are shown in Table 5.

TABLE 5

Inhibition of PMA- and PHA-induced Cytokine Production in Human PBMC Cells.

| | CMPD 2 | CMPD 10 | CMPD 12 | CMPD 20 |
| --- | --- | --- | --- | --- |
| IL-1β | ++ | ++ | ++ | ++ |
| IL-2 | ++ | ++ | ++ | ++ |
| IL-6 | + | ++ | ++ | + |
| IL-8 | − | − | − | − |
| IFN-γ | ++ | ++ | ++ | ++ |
| TNF-α | ++ | ++ | ++ | ++ |
| MIP-1A | + | + | + | + |
| GM-CSF | − | − | − | − |
| G-CSF | − | − | − | − |
| TGF-β1 | − | − | − | − |

Where "−" is no inhibition, "+" is >50% inhibition at 10 µM, "++" is >50% inhibition at 1 µM

Example 8—Effect on Inflammatory Bowel Disease (IBD)/Colitis in Mice

The efficacy of Compound 2 was tested in a dextran sodium sulphate (DSS) induced model of inflammatory bowel disease (IBD)/colitis in female Balb/c mice. Rolipram was used as a positive control in this experiment. Colitis was induced in the mice by providing drinking water containing DSS (3.5%, M. Wt. 30,000-50,000) from Day 0 to Day 8. The test compounds were administered as per their respective groups at specific dose levels starting from Day 0 through to Day 8. Compound 2 was tested at 10 and 30 mg/kg and Rolipram was tested at 5 mg/kg. Colitis was consistently induced in most of the mice, with onset of disease (stool consistency) from Day 2 and drastic reduction in body weight, diarrhea and severe rectal bleeding at Day 5-7 demonstrating the severity of disease. For dosing, Compound 2 was dissolved in vehicle (1.5% Cremophor EL) at 3 mg/mL and 1 mg/mL for the 30 and 10 mg/kg doses, respectively. Rolipram was dissolved in 1% DMSO/99% PBS at 0.5 mg/mL for the 5 mg/kg dose. All doses were administered by oral gavage.

Figure 4:
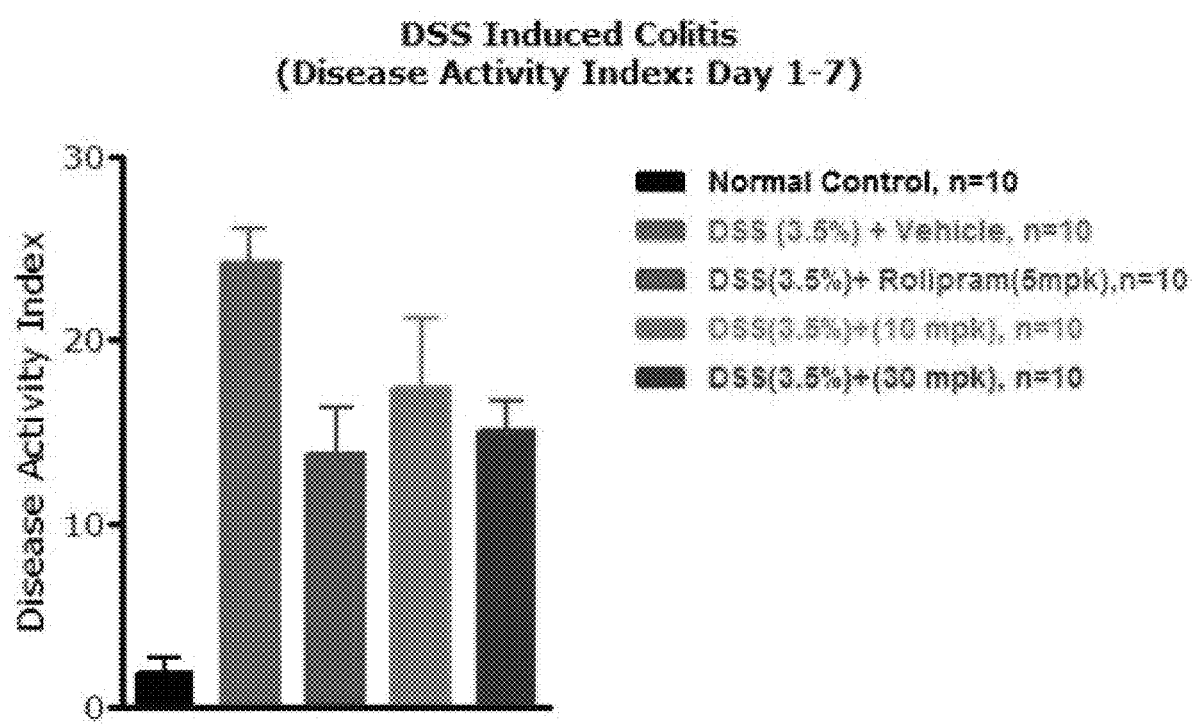
FIG. 4 shows the efficacy of a compound according to an embodiment of the invention in dextran sodium sulphate (DSS)-induced model of inflammatory bowel disease (IBD)/colitis in mice.

There was a considerable increase in disease activity index (DAI) (cumulative scores of body weight, stool consistency and rectal bleeding) in the DSS control group (24.2+5.7) when compared to normal control group (1.9+2.4) which indicated very good disease induction. In treatment groups, Compound 2 at both 10 mg/kg (17.4+12.0) and 30 mg/kg (15.4+4.9) showed very good reduction in DAI when compared to DSS control group (24.2+5.7). The positive control rolipram at 5 mg/kg dose (13.8+8.1) demonstrated very good inhibition on DAI as compared to DSS control group (24.2+5.7). Results are shown in FIG. 4.

Example 9—Efficacy Against the Inflammatory Skin Conditions Psoriasis and Eczema A topical cream containing compound 2 was prepared as follows: Compound 2 was dissolved in propylene glycol at a concentration of 11.0% w/w and this solution was then mixed with the appropriate amount of Glaxal base cream to afford a 1.0% w/w cream of compound 2.

To test the efficacy of this cream against the inflammatory skin conditions psoriasis and eczema, 10 subjects with psoriasis and 5 subjects with eczema were treated with the cream twice daily for a period of 2-12 weeks. Amongst the 10 subjects with psoriasis, 8 of them showed a significant reduction in the skin thickness (induration), erythema and scaling after 8 weeks of treatment. The majority of the subject's lesions were cleared after 12 weeks of treatment. All 5 subjects with eczema responded to the treatment with significantly reduced skin inflammation and pruritis beginning as early as after 2 weeks of treatment.

Example 10—Activating Effects on Aryl Hydrocarbon Receptor (AhR)

This assay was performed using Invitrogen's CellSensor® cell line AhR-CYP1A1-bla LS-180 with GeneBLAzer® Beta-lactamase (bla) Reporter Technology as the detection method. When the AhR-CYP1A1 pathway is activated or inhibited, Beta-lactamase reporter activity is modulated and is measured quantitatively and selectively with the LiveBLAzer™-FRET B/G Loading Substrate.

Briefly, the AhR-CYP1A1-bla LS-180 cells were grown in Growth Media (MEM, 10% FBS, 0.1 mM NEAA, 1 mM Sodium Pyruvate). Cells were dissociated and resuspended in Assay Media (OPTI-MEM, 0.5% dialyzed FBS, 0.1 mM NEAA, 1 mM Sodium Pyruvate). Around $2 \times 10^4$ cells in a volume of 32 µL of assay media was added to each well of a 384 well Poly-D-Lysine assay plate. After incubation for 16 hours at 37° C. in a humidified incubator, 4 µL of a 10× serial dilution of test compounds were added to appropriate wells of the plate. The plate was incubated for 24 hours at 37° C. For the reporter activity assay, 8 µL of 1 µM Substrate was added to each well and the plate was incubated for 2 hours at room temperature. The plate was read on a fluorescence plate reader.

Based on the assay results, an $EC_{50}$ value of 27 nM was determined for Compound 2.

The aryl hydrocarbon receptor (AhR) is a key mechanistic regulator of immunity in both innate and adaptive immune systems (Zhu L., et al, 2016, Trends Immunol, 37(1): 17-31; Shinde et al., 2018, Trends Immunol, 39(12): 1005-1021.). Increased activity of AhR appears to be a common feature of many inflammatory diseases and AhR agonists have been emerged as actionable drug target for immunotherapy.

The ability of the compounds to activate AhR may be beneficial to patients with inflammatory diseases such as asthma, chronic obstructive pulmonary disorder (COPD), psoriasis, inflammatory bowel disease, eczema, and multiple sclerosis.

Example 11—Activating Effects on the Nuclear Erythroid 2-Related Factor 2 (Nrf2)

This assay was performed using INDIGO Bioscience's Nrf2 Reporter Cells which express a native human Nrf2 receptor. The reporter gene, firefly luciferase, is functionally linked to the Gal4 upstream activation sequence (UAS).

Briefly, the Reporter Cells were cultured in DMEM media containing 10% FBS. A cell suspension of Reporter Cells was prepared in Cell Recovery Medium (CRM) containing 10% FBS. The test compounds were prepared in DMSO and were diluted directly into INDIGO's Compound Screening Medium (CSM) containing 10% FBS to generate 2×-concentration treatment media. Then, 100 µl of each prepared treatment medium was dispensed into triplicate assay wells pre-dispensed with a 100 µl suspension of Reporter Cells. Assay plates were incubated for 22-24 hours in a cell culture incubator. Following the incubation period, treatment media were discarded and 100 µl/well of Luciferase Detection Reagent was added. The plate was read on a micro-plate reader.

Based on the assay results, an $EC_{50}$ value of 70 nM was determined for Compound 2.

The transcriptional factor nuclear erythroid 2-related factor 2 (Nrf2) is a master regulator of cellular resistance to oxidants. Nrf2 plays a fundamental role in a cluster of chronic disease pathogenesis which share common mechanisms including oxidative, inflammatory, and metabolic alterations (Cuadrado et al., 2018, Pharmacol Rev, 70:348-383). Extensive work in animal models of experimental autoimmune encephalomyelitis (EAE) and rheumatoid arthritis (RA), clinical evidence in multiple sclerosis (MS) and psoriasis, as well as relevant cell and biological function assays in vitiligo, point to a role of Nrf2 as a therapeutic target for various autoimmune diseases (Cuadrado et al., 2018, Pharmacol Rev, 70:348-383; Jian et al., 2014, J Invest Dermatol, 134(8): 2221-2230; Ma et al., 2018, Free Radical Biol & Med, 129:492-503.). The ability of the compounds to activate Nrf2 may be beneficial to patients suffering from autoimmune diseases such as vitiligo, multiple sclerosis, rheumatoid arthritis, and psoriasis.

Example 12—Effects on Keratinocyte Proliferation

The effects of the test compounds on keratinocyte viability was tested in vitro. The primary human keratinocytes were cultured in EpiLife medium containing the cell growth supplements (HKGS) on tissue culture plates. The cells were treated with different concentrations of the test compounds for 48 hours. Then the keratinocytes were removed from the plates and cell viability was assayed for apoptotic markers (annexin V and propidium iodide) using flow cytometry.

The test compounds were found to be overtly cytotoxic to human keratinocytes at 5-10 µM. Keratinocyte hyperproliferation increases blockage and can promote comedome formation in acne (Tan J et al., 2018, Semin Cutan Med Surg. 37(3S):S60-S62). The ability of the test compounds to induce apoptosis in primary human keratinocytes may contribute to efficacy in acne patients.

Example 13—Effects on IL-17 Cytokine Production in PBMC Cells

Human peripheral blood mononuclear cells (PBMC) were cultured in RPMI 1640 with 10% fetal bovine serum (FBS) at 37° C. in a $CO_2$ incubator. The cells were induced for cytokine production with a combination of PMA and PHA 30 minutes post the compound treatments. Cells were treated with various concentrations of the compounds for 24 hours at 37° C. To determine the cytokine production secreted into the culture medium by PBMC cells, the culture supernatants were collected from compound-treated samples. Commercial ELISA kits (R&D Systems) for both interleukin 17 A and F (IL-17A and IL-17F) were used for the quantitation. The test compounds showed dose dependent inhibitory effects on both IL-17 A and IL-17F production in the PBMC cells.

The TH17 cells are a distinctive lineage of $CD^{4+}$ T cells producing distinctive types of cytokines including IL-17A and IL-17F and are implicated in various inflammatory diseases. The production of IL-17A/F have been shown to play key roles in the pathogenesis of acne and the therapeutic suppression of IL-17A/F production are beneficial to acne patients (Agak et al., 2014, J Invest Dermatol, 134(2): 366-73.). The ability of the test compounds to inhibit the production of IL-17A/F supports that the test compounds would be efficacious for the treatment of skin inflammation conditions that requires IL-17A/F such as acne.

Example 14—Effects on Lung Epithelium Inflammation In Vitro

The compounds were assayed in the Eurofin's BioMap system (BF4T Cells) which models Th2-type lung inflammation, an environment that promotes the recruitment of eosinophils, mast cells, neutrophils, and basophils as well as effector memory T cells. This system is relevant for allergy and asthma, pulmonary fibrosis, as well as chronic obstructive pulmonary disorder (COPD) exacerbations. The human primary bronchial epithelial cells were cultured and stimulated to induce the inflammatory factors responsible for the pathogenesis of various inflammatory diseases in the lung. The test compounds were added to the in vitro model culture system and incubated for 24 hours. The supernatants were collected and assayed for the protein production of various molecules using ELISA assays. The biomarkers assayed included MCP-1, Eotaxin-3, VCAM-1, ICAM-1, CD90, IL-8, IL1α, Keratin 8/18, MMP1, MMP-3, MMP-9, PAI-1, SRB, tPA, and uPA.

Based on the assay results, Compound 2 was found to suppress the production of VCAM-1, ICAM-1, IL-8 and IL-1α in the system.

As those skilled in the art will appreciate, the methods and uses described herein are only examples of many conditions where the invention may be applied to produce therapeutic benefit. Specific pharmacological responses observed may vary according to and depending on the particular active agent(s) and/or pharmaceutical acceptable carrier(s) selected, as well as the type of formulation and mode of administration employed, and such expected variations or differences in the results are contemplated in accordance with practice of the present invention.

What is claimed is:

1. A method of treating an inflammation related disease with a compound having a general formula I, comprising administering to a subject in need thereof a therapeutically effective amount of the compound, the general formula I is shown as following

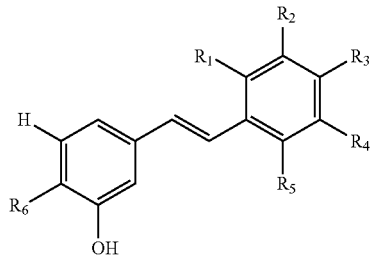

wherein $R^1$ is selected from H, halogen and CN; $R^2$ is selected from H, halogen and CN;
$R^3$ is selected from H, halogen, $OCH_3$ and CN; $R^4$ is H; $R^5$ is selected from H, halogen and CN; and $R^6$ is alkyl or cycloalkyl, wherein the inflammation related disease is selected from a group consisting of an inflammatory bowel disease, psoriasis, atopic dermatitis, asthma, chronic obstructive pulmonary disorder (COPD), multiple sclerosis (MS), vitiligo, rheumatoid arthritis (RA), acne, skin inflammation, and pulmonary fibrosis and wherein the inflammation related disease is characterized by enhanced activity of one or more kinases selected from the group consisting of JAK2, JAK3, p38a, p38O, GSK3, LCK, IKKO and CLK4.

2. The method according to claim 1, wherein the inflammation-related disease is characterized by enhanced expression of one or more cytokines selected from the group consisting of IL-1β, IL-2, IL-6, IFN-γ, TNF-α and MIP-1A.

3. The method according to claim 1, wherein the inflammation-related disease is characterized by enhanced activity of PDE4.

* * * * *